United States Patent
Takamori

(10) Patent No.: US 8,816,687 B2
(45) Date of Patent: Aug. 26, 2014

(54) TOP PLATE FOR MAGNETIC RESONANCE IMAGING APPARATUS, FRAME FOR TOP PLATE SET OF MAGNETIC RESONANCE IMAGING APPARATUS AND MAGNETIC RESONANCE IMAGING APPARATUS

(71) Applicants: Kabushiki Kaisha Toshiba, Tokyo (JP); Toshiba Medical Systems Corporation, Otawara (JP)

(72) Inventor: Hiromitsu Takamori, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

(21) Appl. No.: 13/660,246

(22) Filed: Oct. 25, 2012

(65) Prior Publication Data
US 2013/0057283 A1 Mar. 7, 2013

Related U.S. Application Data

(63) Continuation of application No. PCT/JP2012/058322, filed on Mar. 29, 2012.

(30) Foreign Application Priority Data

Mar. 30, 2011 (JP) ................. 2011-076912

(51) Int. Cl.
*G01V 3/00* (2006.01)
(52) U.S. Cl.
USPC .......................................... 324/318; 324/322
(58) Field of Classification Search
USPC ................. 324/318, 322, 300; 5/600, 601
See application file for complete search history.

(56) References Cited

U.S. PATENT DOCUMENTS

| | | | | |
|---|---|---|---|---|
| 5,475,884 A | * | 12/1995 | Kirmse et al. | 5/601 |
| 5,771,512 A | * | 6/1998 | Kurakake et al. | 5/623 |
| 6,138,302 A | * | 10/2000 | Sashin et al. | 5/600 |
| 6,973,689 B2 | * | 12/2005 | Lenting et al. | 5/601 |
| 7,490,377 B2 | * | 2/2009 | Ahlman | 5/81.1 R |
| 2004/0102690 A1 | | 5/2004 | Bartels et al. | |
| 2008/0267358 A1 | | 10/2008 | Hiyama | |

FOREIGN PATENT DOCUMENTS

JP 2004-525699 8/2004
JP 2008-289854 12/2008

OTHER PUBLICATIONS

International Search Report for PCT/JP2012/058322, mailed Apr. 24, 2012.
Japanese-language Written Opinion of the International Searching Authority for PCT/JP2012/058322, mailed Apr. 24, 2012.
Notification of Transmittal of Translation of the International Preliminary Report on Patentability in PCT/JP2012/058322 mailed Oct. 17, 2013.
Office Action issued Apr. 23, 2014 in on Patent Application No. 201280000411.X.

* cited by examiner

*Primary Examiner* — Louis Arana
(74) *Attorney, Agent, or Firm* — Nixon & Vanderhye PC

(57) ABSTRACT

According to one embodiment, a top plate for a magnetic resonance imaging apparatus includes a placing plate and a supporting part. The placing plate is configured to place an object. The supporting part is provided to the placing plate at a position higher than a position of the placing plate. Further, a frame for a top plate set of a magnetic resonance imaging apparatus according to an embodiment includes a first supporting part and a second supporting part. The first supporting part is configured to support a top plate at a first supporting position. The second supporting part is configured to support the top plate at a second supporting position higher than the first supporting position. Further, a magnetic resonance imaging apparatus according to an embodiment includes the top plate, a bed and an imaging unit.

11 Claims, 9 Drawing Sheets

TOP PLATE FOR MAGNETIC RESONANCE IMAGING APPARATUS, FRAME FOR TOP PLATE SET OF MAGNETIC RESONANCE IMAGING APPARATUS AND MAGNETIC RESONANCE IMAGING APPARATUS

CROSS REFERENCE

This is a continuation of Application PCT/JP2012/058322, filed Mar. 29, 2012.

This application is based upon and claims the benefit of priority from Japanese Patent Application No. 2011-076912, filed Mar. 30, 2011; the entire contents of which are incorporated herein by reference.

FIELD

Embodiments described herein relate generally to a top plate for a magnetic resonance imaging (MRI) apparatus, a frame for a top plate set of a magnetic resonance imaging apparatus, and a magnetic resonance imaging apparatus.

BACKGROUND

MRI is an imaging method which excites nuclear spin of an object set in a static magnetic field with a RF (radio frequency) signal having the Larmor frequency magnetically and reconstructs an image based on NMR (nuclear magnetic resonance) signals generated due to the excitation.

Conventionally, a stretcher has been used as an instrument with which the object is placed on a top plate of a bed in the MRI apparatus. The stretcher is constituted of a top plate with which the object is set and a frame with which the top plate is moved. Then, the top plate of the stretcher is overlapped with the top place of the bed utilizing the frame as the object is placed on the top plate of the stretcher.

Specifically, both sides of the top plate of the stretcher are supported by two arms of the frame at two positions separated by longer distance than the longitudinal width of the top plate of the bed. And one of the two arms, which corresponds to the head side of the object, is arranged in a space between the bed of the MRI apparatus and a gantry. On the other hand, the other of the two arms is arranged on the foot side of the bed. Whereby, the top plate of the stretcher on which the object is placed is arranged separately above the bed.

Next, the position of the top plate of the bed is adjusted by an up-and-down adjuster of the bed such that the height position of the top plate of the bed may be higher than that of the two arms of the frame. Whereby, the top plate of the stretcher is supported by the top plate of the bed such that the frame positioned separately from the top plate of the stretcher is retreated. Then, the top plate on the bed is moved in a state that the top plate of the stretcher is overlapped with the top plate of the bed such that the top plate of the bed, the top plate of the stretcher and the object as a whole are moved into the inside of the gantry.

Recently, the number of RF coils for receiving NMR signals tends to increase with respect to the MRI apparatus. Therefore, a bed having connectors of RF coils on the top plate has become more often employed. It is important to make the thickness of the top plate thinner in order to secure an imaging space and an accommodation space for cables of the connectors with respect to a bed having the connectors. Whereas, it is necessary for the top plate of the bed to have rigidity so as to support the weights of the connectors. As a result, the rigidity of the top plate having the connectors is supposed to be enough rigidity to support the connectors.

When such a top plate having the connectors is employed, it is difficult to arrange the bed at a position separate from the gantry in order to secure enough rigidity of the top plate to support the connectors. That is, it may be more likely to cause an impact of movement as the top plate is moved horizontally if the distance between the bed and the gantry becomes larger.

On the other hand, it is preferable to configure the apparatus such that imaging can be performed in condition where less vibration is caused by shortening the distance between the bed and the gantry even in the case that the bed having the top plate of high rigidity without any connectors. Also, lengthening the distance between the existing gantry and the bed having been installed is subject to restriction of arrangement conditions and remodeling costs.

In addition, it is also possible to downsize the apparatus if the length of the top plate can be shortened, while the rigidity of the top plate is improved.

It is an object of the present invention to provide a top plate having a more appropriate structure for a magnetic resonance imaging apparatus, a frame for a top plate set of a magnetic resonance imaging apparatus and a magnetic resonance imaging apparatus.

PRIOR TECHNICAL LITERATURE

[Patent literature 1] JPA 2007-175239
[Patent literature 2] JPA 2009-082614

DETAILED DESCRIPTION

In general, according to one embodiment, a top plate for a magnetic resonance imaging apparatus includes a placing plate and a supporting part. The placing plate is configured to place an object. The supporting part is provided to the placing plate at a position higher than a position of the placing plate.

Further, a frame for a top plate set of a magnetic resonance imaging apparatus according to an embodiment includes a first supporting part and a second supporting part. The first supporting part is configured to support a top plate at a first supporting position. The second supporting part is configured to support the top plate at a second supporting position higher than the first supporting position.

Further, a magnetic resonance imaging apparatus according to an embodiment includes the top plate, a bed and an imaging unit. The bed is configured to move the top plate on which an object is set into a gantry. The imaging unit is configured to acquire magnetic resonance signals from the object to generate image data of the object by image reconstruction processing of the acquired magnetic resonance signals.

A top plate for a magnetic resonance imaging apparatus, a frame for a top plate set of a magnetic resonance imaging apparatus and a magnetic resonance imaging apparatus according to embodiments of the present invention will now be described with reference to the accompanying drawings.

First Embodiment

Figure 1:
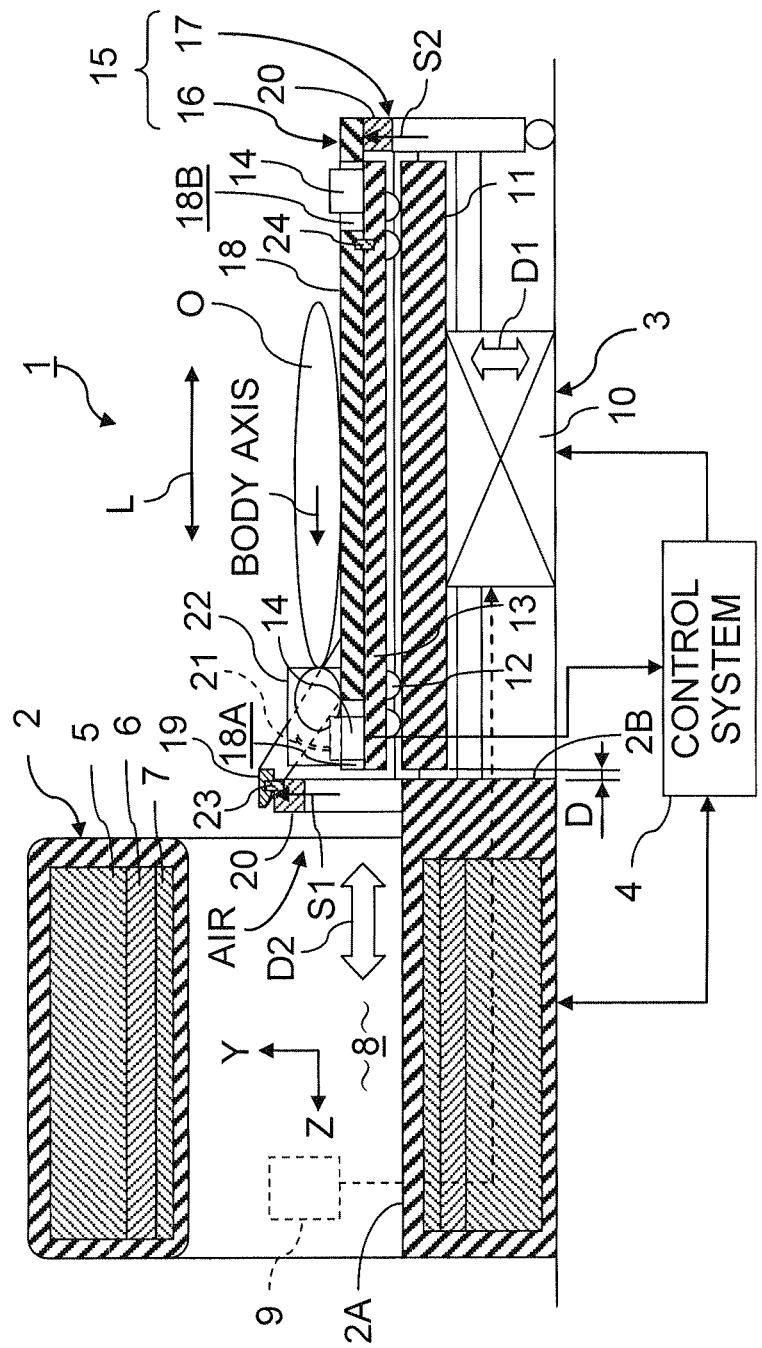
FIG. 1 is a cross section structural diagram showing a magnetic resonance imaging apparatus in which a top plate of a stretcher is set according to the first embodiment of the present invention.
Figure 2:
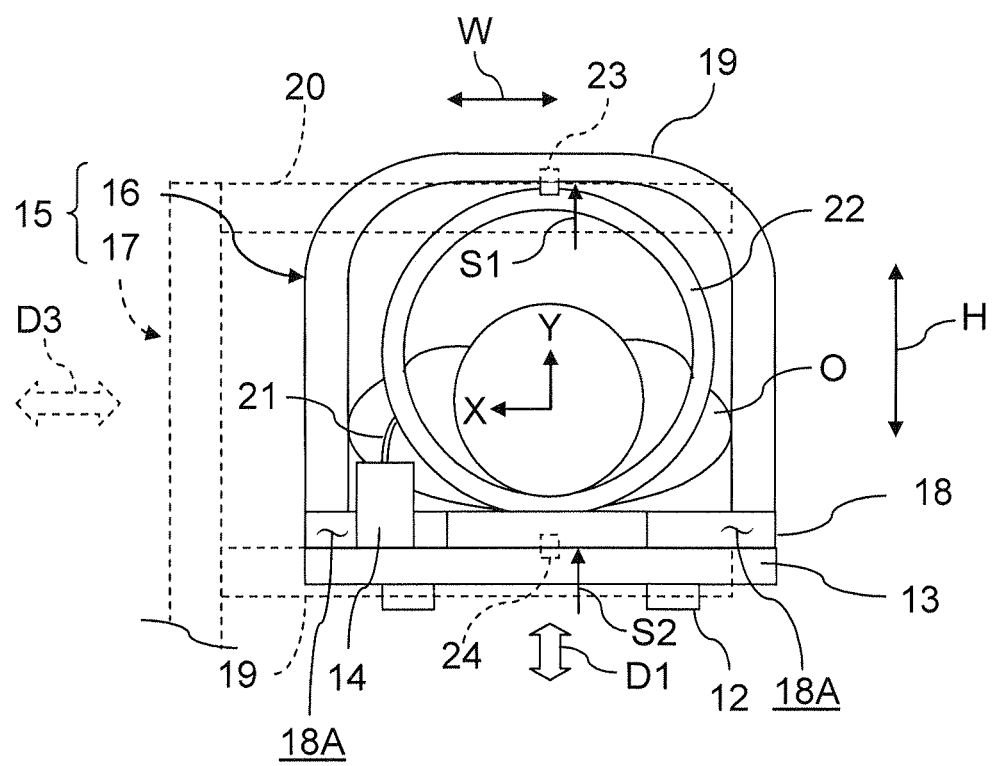
FIG. 2 is a left side view of the top plate of the stretcher shown in FIG. 1.
Figure 3:
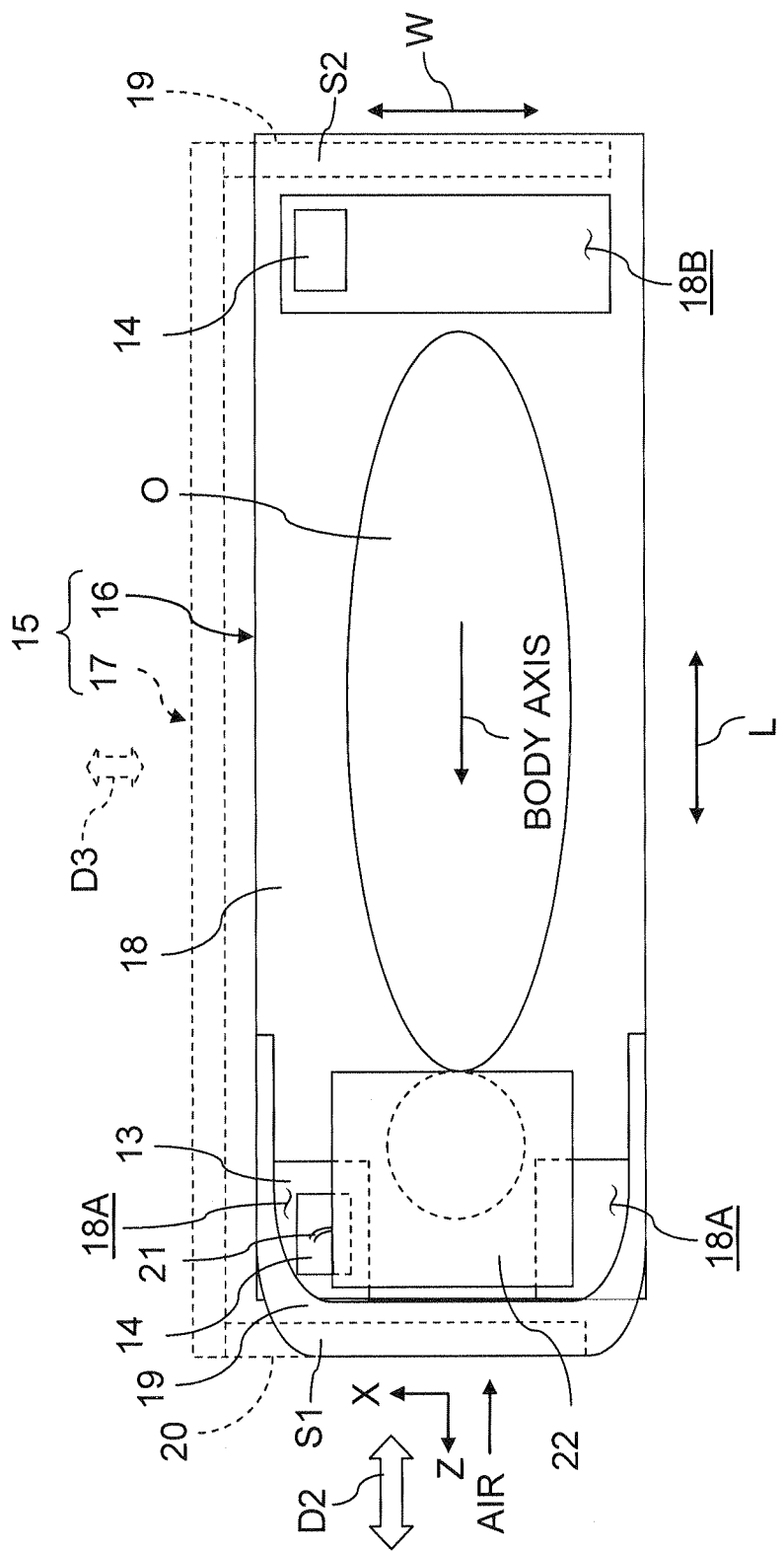
FIG. 3 is a top view of the top plate of the stretcher shown in FIG. 1.

FIG. 1 is a cross section structural diagram showing a magnetic resonance imaging apparatus in which a top plate of a stretcher is set according to the first embodiment of the present invention; FIG. 2 is a left side view thereof in a state that the top plate is set as shown in FIG. 1; and FIG. 3 is a top view thereof in a state that the top plate of the stretcher is set as shown in FIG. 1.

A magnetic resonance imaging apparatus 1 includes a gantry 2, a bed 3 and a control system 4. A static magnetic field magnet 5, a gradient coil 6, and a WB (whole-body) coil 7 each having a cylindrical shape are built into the gantry 2 coaxially. An imaging area 8 is formed as an opening part inside the gantry 2 and an operation panel 9 is arranged at an arbitrary position on the outside.

The static magnetic field magnet 5 is constituted of a superconducting coil or a permanent magnet generating a static magnetic field in the imaging area 8. The gradient coil 6 is constituted of three kinds of coils, which generate magnetic fields in an x-axis direction, a y-axis direction and a z-axis direction perpendicular to each other, respectively such that gradient magnetic fields can be generated in the imaging area 8 by controlling voltages supplied to the three kinds of coils. The WB coil 7 is a RF coil to be mainly used for transmitting RF signals.

Further, the bed 3 is constituted of a bed driving device 10, a fixed top plate 11 and a movable top plate 13 with wheels 12. Connectors 14 are provided on both sides of the movable top plate 13 to connect RF coils for receiving NMR signals. The bed driving device 10 has a function to move the fixed top plate 11 along a moving direction D1 as designated for a vertical direction and a function to move the movable top plate 13 along a moving direction D2 as designated for a horizontal direction between the imaging area 8 inside the gantry 2 and the fixed top plate 11.

Further, the top plate 16 of the stretcher 15 can be placed on the movable top plate 13 by use of the frame 17. The top plate 16 of the stretcher 15 has a placing plate 18 and a supporting part 19. The placing plate 18 is a flat plate member on which the object O is placed and has a shape fitting the movable top plate 13. That is, the longitudinal direction L of the placing plate 18 and the top plate 16 of the stretcher 15 corresponds to a body axis direction of the object O and a moving direction D2 of the movable top plate 13 while a width direction W corresponds to a direction perpendicular to a coronal plane of the object O. Further, a height direction H of the top plate 16 of the stretcher 15 and a thickness direction of the placing plate 18 correspond to an up-and-down driving direction D1 of the fixed top plate 11 perpendicular to a sagittal plane of the object O.

The supporting part 19 is fixed to one end of the placing plate 18 in the longitudinal direction L, which is the gantry 2 side. The supporting part 19 has a supporting plane forming the first supporting position S1 at a position higher than that of the placing plate 18. Therefore, the supporting plane forming the first supporting position S1 faces the placing plate 18 side. In addition, it is desirable that the supporting part 19 is formed such that the first supporting position S1 is located outer than the end part, corresponding to the gantry 2 side, of the placing plate 18 in the longitudinal direction L.

Hence, the supporting part 19 is supposed to be in a shape rising obliquely if viewed from the width direction W of the placing plate 18 and the top plate 16 as shown in FIGS. 1 to 3 for example.

On the other hand, the supporting plane is formed on a face, on a side where the object O is not placed, at the other end, on a side where the supporting part 19 is not provided, of the placing plate 18 in the longitudinal direction L. Thus, the top plate 16 of the stretcher 15 can be traveled by supporting the top plate 16 at the first supporting position S1 formed on the supporting part 19 and at the second supporting position S2 formed on the rear face at the end part of the placing plate 18.

A frame 17 can be utilized as a tool to move the top plate 16. The frame 17 has two bar-shaped arms 20 disposed at different height positions. The two bar-shaped arms 20 are fixed to the frame 17 according to the first supporting position S1 and the second supporting position S2 such that the supporting part 19 of the top plate 16 and the end part of the placing plate 18 may be supported at the first supporting position S1 and the second supporting position S2, respectively.

The top plate 16 can be mounted on and demounted from the movable top plate 13 with the frame 17. The first supporting position S1 formed by the supporting part 19 becomes higher than the position of the lowest part 2A of the opening part forming the imaging area 8 of the gantry 2 in a state that the top plate 16 has been set on the movable top plate 13. Further, the first supporting position S1 formed by the supporting part 19 becomes closer to the center side of the gantry 2 than a face 2B on the bed 3 side of the gantry 2.

Therefore, the supporting part 19 of the top plate 16 positioned higher than the lowest part 2A of the opening part of the gantry 2 can be supported at the first supporting position S1 by the arm 20 even if a gap D of the movable top plate 13 and the fixed top plate 11 of the bed 3 from the face 2B on the bed 3 side of the gantry 2 is made narrow. In other words, the arm 20 for supporting the top plate 16 on the gantry 2 side can be arranged by utilizing an upper space from the bed 3 even if the gap D between the gantry 2 and the bed 3 is made narrow.

In particular, the lower part forming the lowest part 2A at the opening part of the gantry 2 is often formed to have the face 2B projecting toward the bed 3 side compared to the upper part of the gantry 2 in order to secure necessary rigidity to support the hardware such as the gradient coil 6 and the like. In such a case, the upper space of the projecting lower part of the gantry 2 can be even more effectively utilized by arranging the first supporting position S1 of the top plate 16 closer to the center side of the gantry than the face 2B on the bed 3 side of the gantry 2.

Further, the top plate 16 of the stretcher 15 has such a structure that the top plate 16 would not interfere with the connector 14 on the movable top plate 13 and the RF coil for receiving signals connected to the connector 14 when the top plate 16 is set on the movable top plate 13 of the bed 3.

For example, interference avoidance parts including an opening part 18B and a notch 18A to avoid the interference with the connectors 14 provided on both sides of the movable top plate 13 are provided with the placing plate 18. That is, the interference avoidance parts are provided onto the placing plate 18 so as to correspond to positions of the connectors 14 on the movable top plate 13 as shown in FIGS. 1 to 3. FIGS. 1 to 3 show an example in which notches 18A are provided at both corners on the end part on the supporting part 19 side of the placing plate 18 while an opening part 18B is provided near the other end part of the placing plate 18.

It is also possible to configure the shape of the supporting part 19 in a structure that can avoid the interference with the connectors 14 and the RF coil for receiving signals. FIGS. 1 to 3 show an example in which the RF coil 22 for the head is connected as the RF coil for receiving NMR signals through a cable 21 to the connector 13 on the gantry 2 side of the movable top plate 12. That is, the head of the object O is covered with the RF coil 22 for the head.

Accordingly, as shown in FIG. 3, the shape of the supporting part 19 can be formed into an arch-like shape having an apex in an end part side of the placing plate 18 as viewed from a thickness direction of the placing plate 18 and a height direction H of the top plate 16. Hence, when the RF coil 22 for the head is set on the head part of the object O, the supporting part 19 having the arch-like shape is arranged such that the RF coil 22 for the head and the connectors 14 are surrounded. That is, the top plate 16 of the stretcher 15 can be set on the movable top plate 13 of the bed 3 without interference with the RF coil 22 for the head and the connectors 14.

Further, as shown in FIG. 2, the shape of the supporting part 19 can be formed into an arch-like shape having the highest part as an apex as viewed from the longitudinal direction L of the placing plate 18 and the top plate 16. Hence, the RF coil 22 for the head is easily mounted to and demounted from the connectors 14. That is, a gap formed between the supporting part 19 and the placing plate 18 can be utilized as a space such that the RF coil 22 for the head may be mounted to and demounted from the connectors 14.

Figure 4:
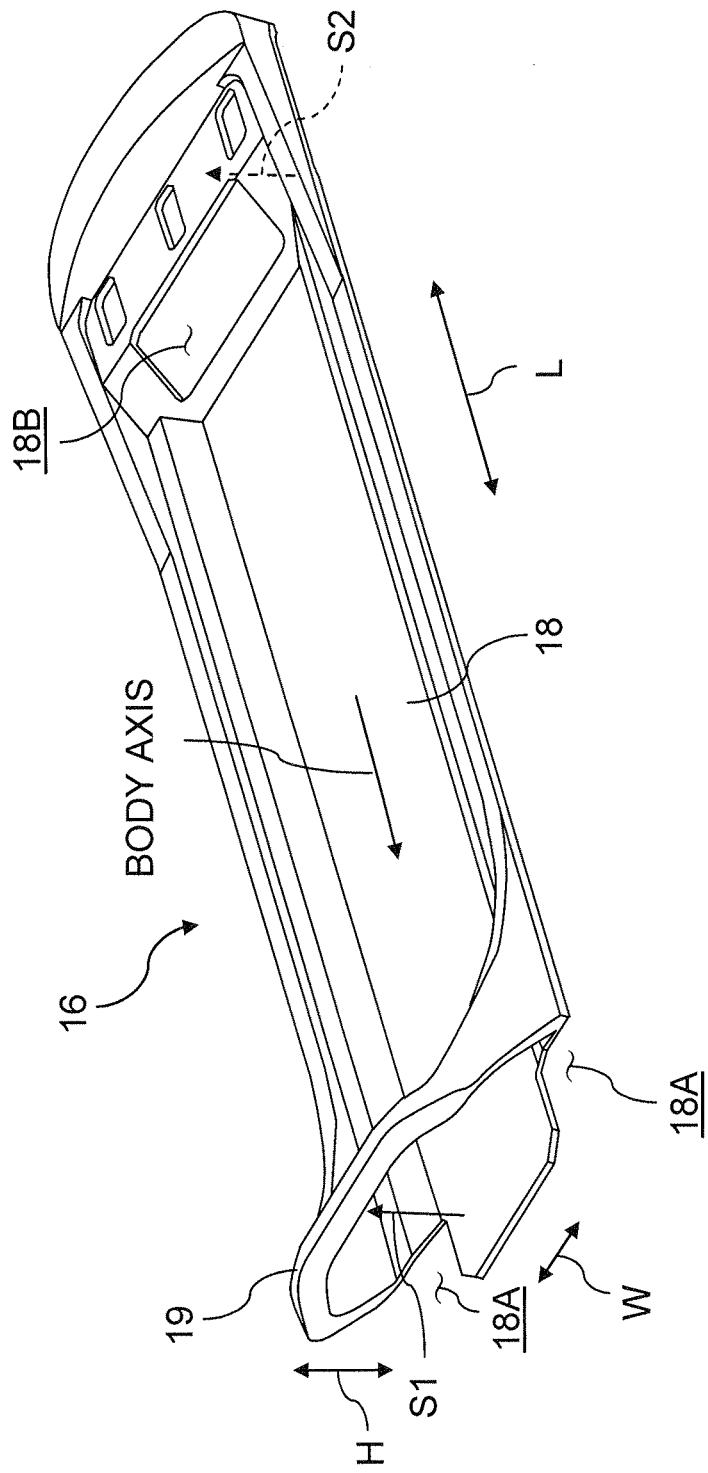
FIG. 4 is a perspective view showing a concrete structural example of the top plate of the stretcher shown in FIG. 1.

FIG. 4 is a perspective view showing a concrete structural example of the top plate 16 of the stretcher 15 shown in FIG. 1.

As shown in FIG. 4, the top plate 16 of the stretcher 15 has the placing plate 18 and the supporting part 19. The supporting part 19 is integrally fixed to one end in the longitudinal direction L of the placing plate 18 corresponding to the body axis direction of the object O. Then, the supporting part 19 has the first supporting position S1 at a position higher than the placing plate 18. Therefore, the supporting part 19 is formed into an obliquely rising shape as viewed from the width direction W of the placing plate 18 and the top plate 16.

On the other hand, the second supporting position S2 is formed on a reverse face of the end part, where the supporting part 19 is not disposed, of the placing plate 18. Further, the placing plate 18 has notches 18A and an opening part 18B so as not to interfere with the connectors 14 disposed to the movable top plate 13.

Figure 5:
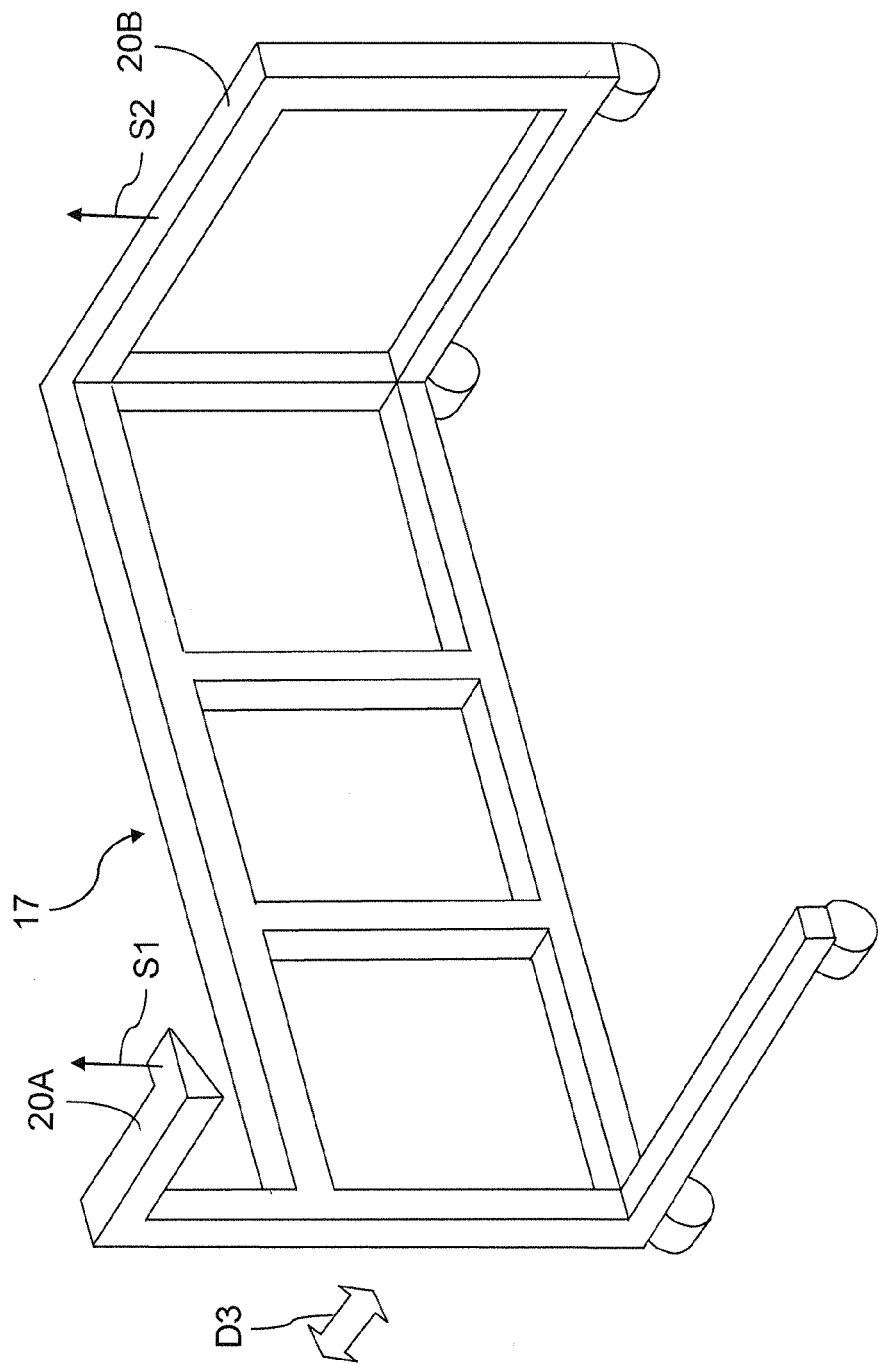
FIG. 5 is a perspective view showing a structural example of a frame with which the top plate shown in FIG. 4 is set on the bed.

FIG. 5 is a perspective view showing a structural example of a frame 17 with which the top plate 16 shown in FIG. 4 is set on the bed 3.

As shown in FIG. 5, the structure of the frame 17 is formed in such a structure corresponding to the structure of the supporting part 19. Specifically, the frame 17 has two arms 20A and 20B having mutually different heights so as to correspond to the first supporting position S1 and the second supporting position S2. That is, the frame 17 has a structure including the arm 20A to work as the first supporting part in order to support the top plate 16 at the first supporting position S1 and the arm 20B to work as the second supporting part in order to support the top plate 16 at the second supporting position S2 which is lower than the first supporting position S1. Then, by supporting the top plate 16 at the two positions with the arms 20A and 20B, the top plate 16 can be moved with use of the frame 17.

Further, the structure of the arm 20A to work at least as the first supporting part is formed in a cantilever structure. The arm 20A to work as the first supporting part has a reversed L-letter shape in the example as shown in FIG. 5. According to this, the arm 20 can be retracted from the top plate 16 by moving the frame 17 in the moving direction D3. Here, a rotational mechanism may be provided to the frame 17 such that the arm 20 can be rotated in the horizontal direction and the arm 20 may be retracted from the top plate 16 by the rotation of the arm 20. Alternatively, only the arm 20 may be configured to be retracted in the moving direction D3.

To the top plate 16 of the stretcher 15 having such a structure, positioning on the movable top plate 13 of the bed 3 can be performed with ease by utilizing the frame 17 in a state that the RF coil 22 for the head and the object O are set on the placing plate 18 even if the gap D between the gantry 2 and the bed 3 is small.

Specifically, the fixed top plate 11 of the bed 3 is moved downward along the moving direction D1 in advance by driving the bed driving device 10. Hence, the fixed top plate 11 and the movable top plate 13 are arranged at positions low enough. That is, at least the fixed top plate 11 is arranged into a position lower than the lowest part 2A of the opening part of the gantry 2.

On the other hand, the top plate 16 of the stretcher 15 is supported at the first supporting position S1 and the second supporting position S2 by the two arms 20 of the frame 17. A switch 23 to detect whether the top plate 16 has applied its weight to the frame 17 or not and whether the arm 20 has been retracted from the top plate 16 or not is provided at an arbitrary position of the frame 17 or the top plate 16 of the stretcher 15. FIGS. 1 and 2 show an example where the switch 23 is provided to a part of the supporting part 19 which is contacted and supported by the arm 20 of the frame 17. Hence, the switch 23 is turned in an ON-state by having the arm 20 support the top plate 16.

Next, the RF coil 22 for the head and the object O are set on the placing plate 18. Then, the frame 17 having supported the top plate 16 of the stretcher 15 is moved along the moving direction D3 which crosses the moving direction D2 of the movable top plate 13 of the bed 3 and is positioned above the movable top plate 13. Next, the fixed top plate 11 is moved upward along the moving direction D1 by driving the bed driving device 10. Hence, when the fixed top plate 11 reaches the lowest part 2A of the opening part of the gantry 2, the movable top plate 13 contacts the placing plate 18 of the stretcher 15 and the weight of the top plate 16 moves from the frame 17 to the movable top plate 13.

A switch 24 to recognize whether the top plate 16 has been set on the movable top plate 13 or not is provided at an arbitrary position of the movable top plate 13 or the top plate 16. FIGS. 1 and 2 show an example in which the switch 24 has been provided to a part that contacts the top plate 16 of the movable top plate 13. Hence, the weight of the top plate 16 moves from the frame 17 to the movable top plate 13 such that the switch 24 is turned to the ON-state.

Further, the RF coil 22 for the head is connected to the connectors 14 provided on the movable top plate 13 through the cable 21.

Next, the frame 17 is moved in the moving direction D3 of the frame 17 to be retracted. Therefore, the arm 20 leaves the top plate 16 and is retracted such that the switch 23 to recognize whether the top plate 16 is mounted to or demounted from the frame 17 and whether the arm 20 is retracted or not is turned then to its OFF-state. Hence, the preparation of imaging the object O is completed.

The switch 23 to recognize whether the top plate 16 is mounted to or demounted from the frame 17 and whether the arm 20 is retracted or not, and the switch 24 to recognize whether the top plate 16 of the stretcher 15 is mounted to or demounted from the movable top plate 13 are connected to the operation panel 9 of the gantry 2 through the wiring. When the top plate 16 of the stretcher 15 has been demounted from the arm 20 of the frame 17 to retract the arm 20 and signals to indicate that the top plate 16 has been set on the movable top plate 13 are output from the switch 23 and the switch 24 to the operation panel 9, it becomes possible to move the movable top plate 13, on which the top plate 16 of the stretcher 15 has been set, into the imaging area 8 of the gantry 2 by the operation of the operation panel 9.

That is, the bed driving device 10 is controlled by the operation of the operation panel 9. Then, the bed driving device 10 moves the movable top plate 13 in the moving direction D2 such that the movable top plate 13 is sent into the imaging area 8 in the gantry 2. Hence, the top plate 16, on which the RF coil 22 for the head and the object O has been set, is sent into the imaging area 8 in the gantry 2 together with the movable top plate 13.

A fin may be formed on the supporting part 19 of the top plate 16 so that wind from a fan arranged on an opposite side to the bed in the gantry 2 may be directed to the object O side.

Figure 6:
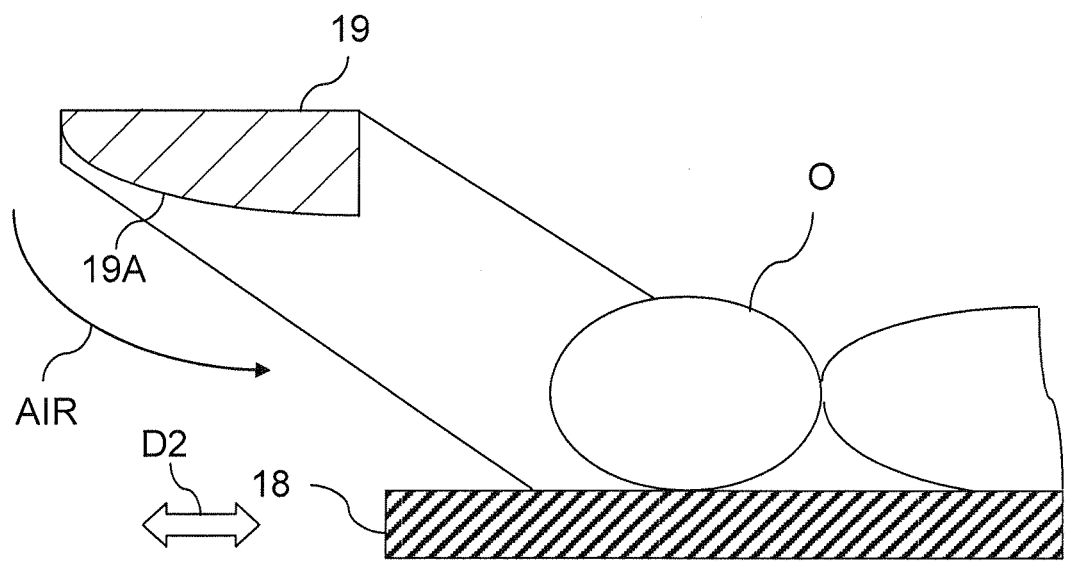
FIG. 6 is an enlarged cross section view of a fin formed onto the supporting part of the top plate shown in FIG. 1.

FIG. 6 is an enlarged cross section view of a fin formed onto the supporting part 19 of the top plate 16 shown in FIG. 1.

FIGS. 1 and 6 show an example in which the fin is formed by providing a face 19A, having a slope toward the placing plate 18 side, on the supporting part 19. That is, as shown in FIGS. 1 and 6, the shape of cross section of the supporting part 19 in the direction perpendicular to the width direction W of the placing plate 18 may be a shape having the slope for guiding wind toward the object O in the RF coil 22 for the head when the movable top plate 13 is moved. Hence, an air flow toward the object O can be created so that the object O may be provided with refreshed feeling while the movable top plate 13 is moved along the moving direction D2.

Then, when the top plate 16, on which the RF coil 22 for the head and the object O has been set, is arranged in the imaging area 8 in the gantry 2, it becomes possible to start imaging of the object O.

The control system 4 has a function to acquire NMR signals from the object O in accordance with the imaging conditions by controlling the hardware including the static magnetic field magnet 5, the gradient coil 6, the WB coil 7, the RF coil for receiving signals and the bed driving device 10 and a function to generate MR image data of the object O by data processing including image reconstruction processing with respect to the acquired NMR signals. That is, the control system 4 and the hardware including the static magnetic field magnet 5, the gradient coil 6, the WB coil 7, the RF coil for receiving signals and the bed driving device 10 give a function as an imaging unit, performing imaging of the object O, to the magnetic resonance imaging apparatus 1.

Then, when the control system 4 outputs a control signal to each element, the static magnetic field magnet 5 and the gradient coil 6 generate a static magnetic field and a gradient magnetic field in the imaging area 8 and the WB coil 7 transmits a RF magnetic field pulse toward the object O. Consequently, NMR signals generated in the object O are received by the RF coil 22 for the head. The RF coil 22 for the head outputs the received NMR signals to the control system 4 though the cable 21 and the connector 14 on the movable top plate 13.

Thus, the control system 4 can create MR image data in the head part of the object O by data processing with respect to the NMR signals. Then, the created MR image data is provided for diagnosis.

That is, with respect to the top plate 16 of the stretcher 15 as described above, the supporting position thereof in the head part side of the object O is configured to be higher than the lowest part 2A of the opening part of the gantry 2 such that the arm 20 of the frame 17 can support the top plate 16 even if the gap D between the gantry 2 and the bed 3 is small.

Therefore, the top plate 16 of the stretcher 15 as described above can be set on the fixed top plate 11 of the bed 3 by utilizing the fragment 17 without providing a big gap between the gantry 2 and the bed 3 of the magnetic resonance imaging apparatus 1. In particular, the top plate 16 can be set on the fixed top plate 11 by utilizing the frame 17 in a state where the bed 3 is brought close to the gantry 2 even if the bed 3 has the connectors 14 on the fixed top plate 11 requiring rigid securement. As a result of this, imaging of the object O can be performed in a stable condition with less impact by the magnetic resonance imaging apparatus 1 utilizing the top plate 16 as described above.

Further, the top plate 16 of the stretcher 15 has a structure without any interference with the RF coil for receiving signals and the connectors 14 on the movable top plate 13 on the bed 3 side. Hence, the top plate 16 can apply not only to a bed without any connectors for RF coils, but also to the bed 3 having the connectors 14 for the RF coil.

Modification of First Embodiment

The shape, the number and the position of the supporting part 19 of the top plate 16 may be made different from those shown in FIGS. 1 to 4.

Figure 7:
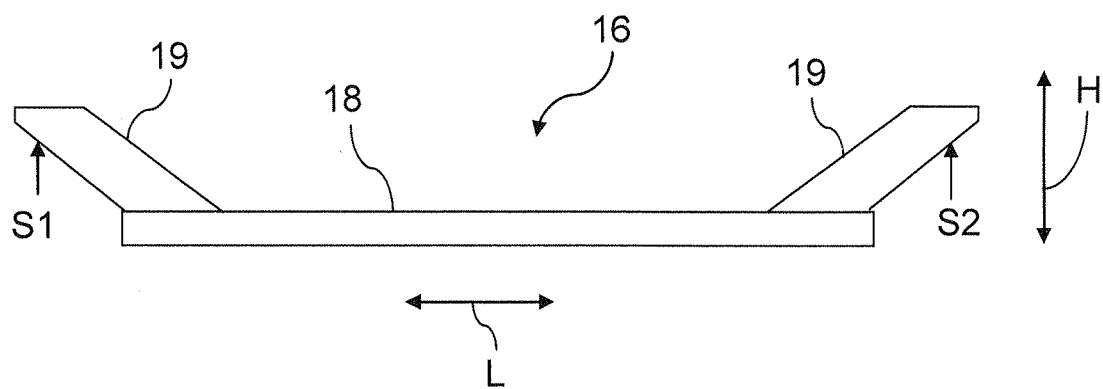
FIG. 7 is a structural diagram showing a first modified example of the supporting part of the top plate shown in FIG. 1.

FIG. 7 is a structural diagram showing a first modified example of the supporting part 19 of the top plate 16 shown in FIG. 1.

As shown in FIG. 7, the top plate 16 can be configured by being provided with supporting parts 19, each having an arch-like shape, on both end parts of the placing plate 18 in the longitudinal direction. If the top plate 16 is configured in this way, the structure of the frame 17 can be simplified by making the first supporting position S1 and the second supporting position S2 have a same height. In addition, the top plate 16 can be moved stably by the frame 17 since the top plate 16 is supported at two positions of the first supporting position S1 and the second supporting position S2 apart from the center of gravity of the placing plate 18.

Figure 8:
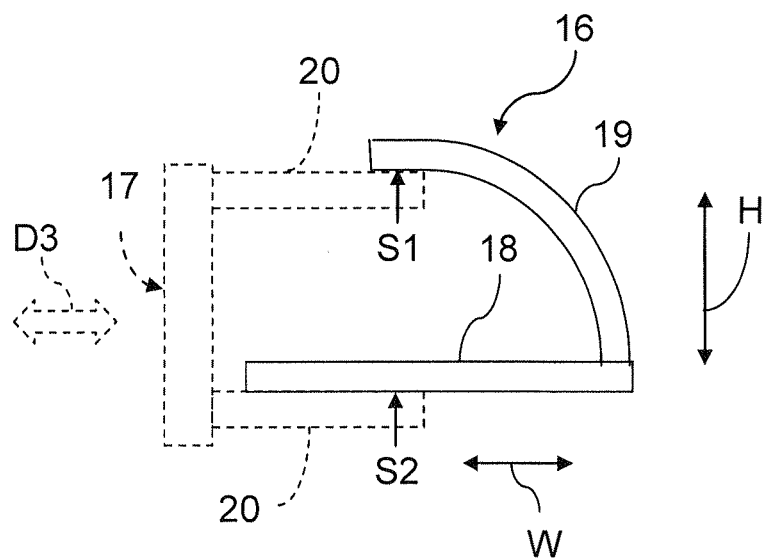
FIG. 8 is a structural diagram showing a second modified example of the supporting part of the top plate shown in FIG. 1.

FIG. 8 is a structural diagram showing a second modified example of the supporting part 19 of the top plate 16 shown in FIG. 1.

As shown in FIG. 8, the top plate 16 can be also configured by providing a supporting part 19 having a shape different from an arch shape to the placing plate 18. FIG. 8 shows an example in which the supporting part 19 having a C-shaped arm structure, as viewed from the longitudinal direction L of the placing plate 18, is provided to an end part on the gantry 2 side of the placing plate 18. When the supporting part 19 is configured in this way, the arm 20 can be easily retracted and the RF coil 22 for the head can be easily set since the interference of the supporting part 19 with any other structural objects is more surely prevented. It is also possible to arrange plural supporting parts 19, each having a C-shaped arm structure, on desired positions of the placing plate 18.

Second Embodiment

Figure 9:
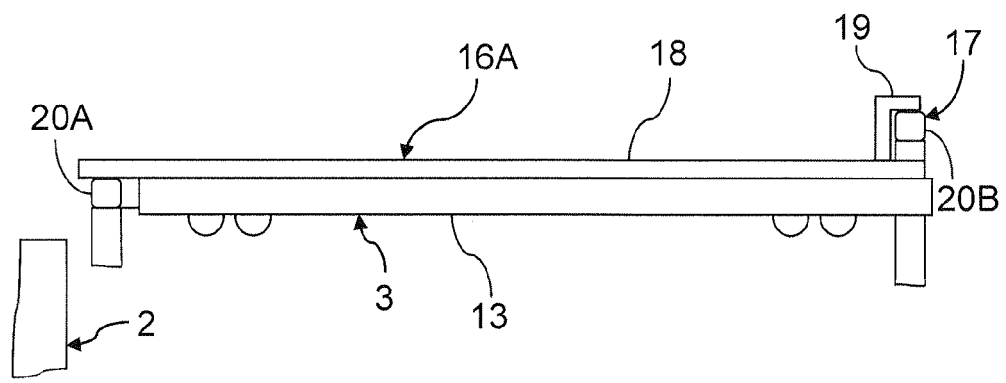
FIG. 9 is a front view of a top plate of a stretcher according to the second embodiment of the present invention.
Figure 10:
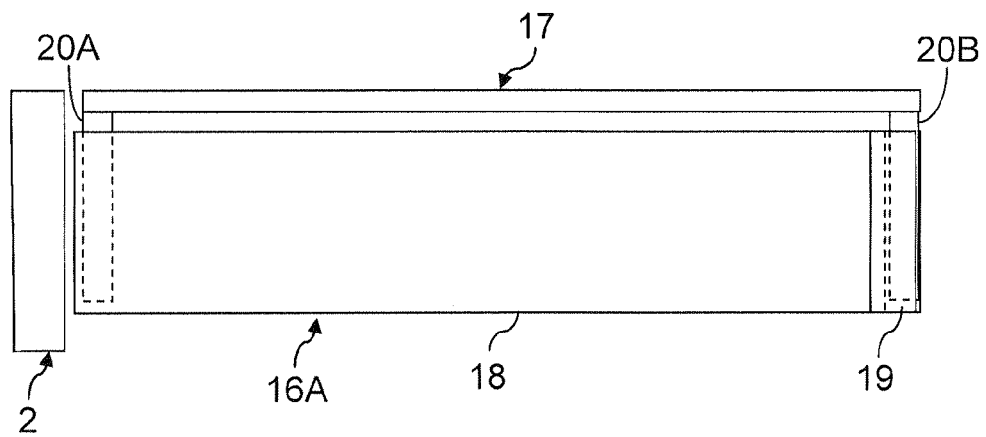
FIG. 10 is a top view of the top plate shown in FIG. 9.

FIG. 9 is a front view of a top plate of a stretcher according to the second embodiment of the present invention. FIG. 10 is a top view of the top plate 16A shown in FIG. 9.

With respect to a top plate 16A in the second embodiment, the structure and the position of the supporting part 19 are different from those of the top plate 16 in the first embodiment. The other configurations and functions thereof are the same as those of the top plate 16 in the first embodiment. Therefore, only the structure and the position of the supporting part 19 will be explained and explanation of the other configurations and functions will be omitted.

FIGS. 9 and 10 show a state in which the top plate 16A has been set on the movable top plate 13 of the bed 3 by utilizing the frame 17 having two arms 20A and 20B. As shown in FIGS. 9 and 10, the supporting part 19 can be arranged inside from the end part of the placing plate 18 in the longitudinal direction on the opposite side to the gantry 2. Therefore, the supporting position of the supporting part 19 on the opposite side to the gantry 2 is higher than the position of the placing plate 18.

According to the example shown in FIGS. 9 and 10, the supporting part 19 is configured to have a structure in which two plate members are jointed at a right angle. That is, the supporting part 19 is constituted of a plate member having a cross section in a reversed L-letter shape.

Figure 11:
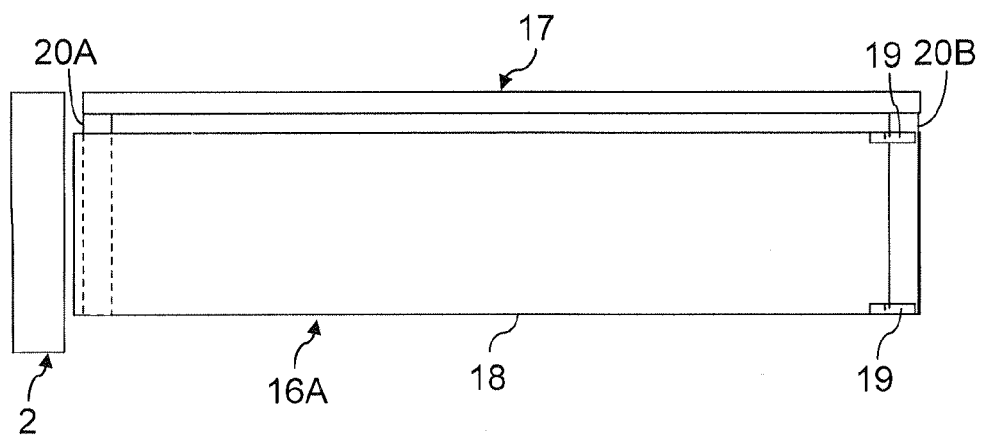
FIG. 11 is a top view showing a modified example of the top plate shown in FIG. 10.

FIG. 11 is a top view showing a modified example of the top plate 16A shown in FIG. 10.

As far as the supporting position is inside from the end part in the longitudinal direction of the placing plate 18, not only the example as shown in FIG. 10, but also other various structures can be applied to the supporting part 19. For example, two bars or plates each having the reversed L-letter shape as shown in FIG. 11 can be fixed to the end part on the opposite side to the gantry 2 of the placing plate 18 as the supporting parts 19.

Figure 12:
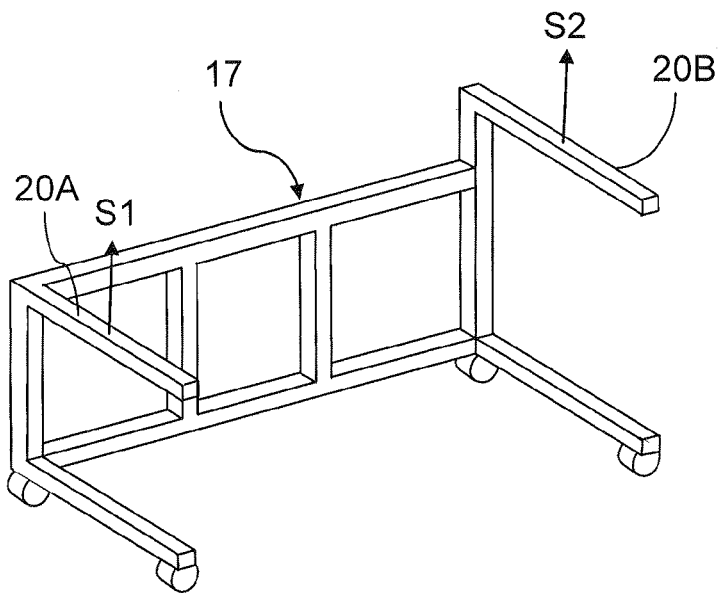
FIG. 12 is a perspective view showing a structure of a frame for the top plate shown in FIG. 9.

FIG. 12 is a perspective view showing a structure of a frame 17 for the top plate 16A shown in FIG. 9.

When the supporting part 19 is configured to be in such a structure, the structure of the frame 17 becomes a structure corresponding to the structure of the supporting part 19. Specifically, the frame 17 is formed in a structure including two arms 20A and 20B having mutually different heights as shown in FIG. 12. In this case, one arm 20A works as the first supporting part to support the top plate 16A at the first supporting position S1. Meanwhile, the other arm 20B works as the second supporting part to support the top plate 16A at the second supporting position S2, which is higher than the first supporting position S1.

When the structure of the arm 20B working as the second supporting part is made in a cantilever structure at least, the frame 17 can be retracted after the top plate 16A is set to the movable top plate 13 of the bed 3 from one direction by utilizing the frame 17. In the example as shown in FIG. 12, the arm 20B to work as the second supporting part has a reversed L-letter shape.

According to the top plate 16A in such second embodiment, the reverse face of the end part of the placing plate 18 on the opposite side to the gantry 2 is not to be a supported face by the frame 17. Therefore, the placing plate 18 can be set on the movable top plate 13 of the bed 3 by utilizing the frame 17 without having the placing plate 18 project in the longitudinal direction of the movable top plate 13. As a result of this, the top plate 16A can be shortened so as to make the top plate 16A compact.

Note that, as in the same way of the first embodiment, a flow adjusting mechanism to form an air flow toward the object O can also be provided to the supporting part 19 in the second embodiment.

Modification of Second Embodiment

Figure 13:
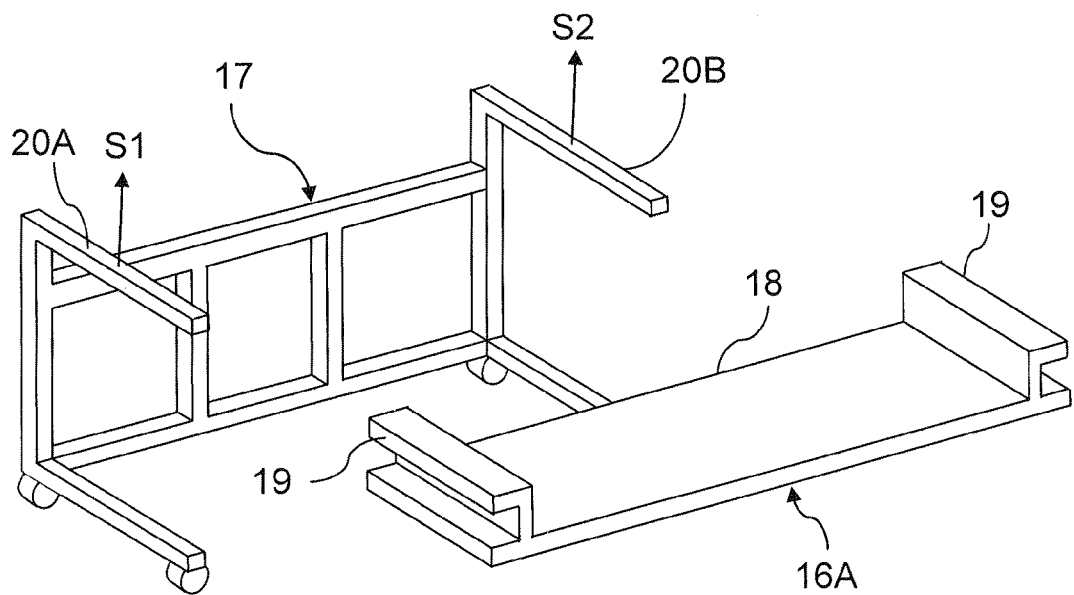
FIG. 13 is a structural diagram showing a modified example of the frame and the top plate shown in FIG. 9.

FIG. 13 is a structural diagram showing a modified example of the frame 17 and the top plate 16A shown in FIG. 9.

In the second embodiment, the top plate 16A also can be configured by arranging supporting parts 19 on both end parts respectively in the longitudinal direction of the placing plate 18. If the top plate 16A is configured in this way, the two arms 20A and 20B can have a same height such that the structure of the frame 17 can be simplified.

Not limited to the example shown in FIG. 13, the supporting part 19 may also be arranged only in the gantry 2 side of the placing plate 18. That is, the top plate 16A can be configured by providing the supporting part 19 to at least one of both ends of the placing plate 18 such that the supporting position is located inside from the end part in the longitudinal direction of the placing plate 18. In this way, the top plate 16A can be shortened so as to become compact.

Other Embodiments

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A top plate for a magnetic resonance imaging (MRI) apparatus which MRI apparatus includes a connector for a radio frequency coil to be coupled to an object to be imaged that is supported by said top plate, said top plate comprising:
    a placing plate configured to place an object to be imaged thereon; and
    a supporting part provided on said placing plate at a position higher than a position of said placing plate on which the object is to be placed,
    wherein said placing plate has a notch or an opening part configured to avoid interference with said connector for a radio frequency coil when positioned on said MRI apparatus.

2. A top plate for a magnetic resonance imaging apparatus of claim 1,
    wherein said supporting part is formed so as to have a supporting position outside an end part of said placing plate in a longitudinal direction of said placing plate.

3. A top plate for a magnetic resonance imaging apparatus of claim 1, wherein said supporting part is formed so as to have a supporting position inside an end part of said placing plate in a longitudinal direction of said placing plate.

4. A top plate for a magnetic resonance imaging apparatus of claim 1,
wherein said supporting part is formed in an arch shape as viewed from a longitudinal direction of said placing plate.

5. A top plate for a magnetic resonance imaging apparatus of claim 1,
wherein said supporting part is provided to one end of said placing plate in a longitudinal direction of said placing plate; and
said placing plate has a supporting face formed on a face on a side where the object is not placed, the supporting face forming at another end in the longitudinal direction of said placing plate.

6. A top plate for a magnetic resonance imaging apparatus of claim 1,
wherein said supporting part is provided to each of both ends of said placing plate in a longitudinal direction of said placing plate.

7. A top plate for a magnetic resonance imaging apparatus of claim 1,
wherein said supporting part is formed in an arch shape having an apex on an end part side of said placing plate as viewed from a thickness direction of said placing plate.

8. A magnetic resonance imaging apparatus comprising:
a top plate of claim 1;
a bed configured to move the top plate on which an object is set into a gantry; and
an imaging unit configured to acquire magnetic resonance signals from the object to generate image data of the object by image reconstruction processing of the acquired magnetic resonance signals.

9. A magnetic resonance imaging apparatus of claim 8,
wherein said imaging unit is configured to receive the magnetic resonance signals with a radio frequency coil connected to a connector provided on said bed.

10. A frame for supporting longitudinally opposite ends of a top plate set of a magnetic resonance imaging apparatus wherein said top plate set is configured to support a patient and includes a transverse support arch at one end thereof, said frame comprising:
a first arm having a first length configured to support said top plate set at a first end supporting position; and
a second arm having a second length configured to support the top plate set at a second end supporting position higher than the first end supporting position, said second arm length being shorter than the first arm length and configured to support a second end supporting position of said top plate set at a mid-point of said transverse support arch.

11. A frame for a top plate set of a magnetic resonance imaging apparatus of claim 10,
wherein said second arm has a cantilever structure.

* * * * *